United States Patent [19]

Bush et al.

[11] 4,036,698

[45] July 19, 1977

[54] METHOD AND APPARATUS FOR MEMBRANE FILTER STERILITY TESTING

[75] Inventors: John H. Bush, Weston, Mass.; Jean Lemonnier, Le Vesinet, France

[73] Assignee: Millipore Corporation, Bedford, Mass.

[21] Appl. No.: 521,251

[22] Filed: Nov. 6, 1974

[51] Int. Cl.² ............................. C12K 1/04; C12K 1/10
[52] U.S. Cl. ............................... 195/103.5 M; 195/127
[58] Field of Search ........ 195/127, 103.5 R, 103.5 M; 23/230 B, 253 R; 21/91, 82 R

[56] References Cited

U.S. PATENT DOCUMENTS 3,448,011  6/1969  Russomanno ................ 195/103.5 R

OTHER PUBLICATIONS

"Analyzing Air and Water Pollution with Millipore Filters" catalog No. ANE01, Millipore Corporation, Beford, Mass. 01730.

*Primary Examiner*—Alvin E. Tanenholtz
*Assistant Examiner*—C. A. Fan
*Attorney, Agent, or Firm*—Kenway & Jenney

[57] ABSTRACT

A method and apparatus for testing of solutions, such as antibiotic solutions to determine the presence of microorganisms, in which the solution is flowed through a plastic cylinder having a microporous membrane filter which strains microorganisms from the solution and concentrates them on the filter and thereafter the cylinder is flushed with a sterile solution, followed by filling the cylinder with an appropriate growth culture medium with the filter being vented, during this step, through a vent having a hydrophobic filter to prevent intake of bacteria. The presence of microorganisms in the original solution to be tested is determined by visual observation of the turbidity of the growth solution after an appropriate incubation period at suitable temperature. Where more than one microorganism is being tested for, aliquots of the test solution are flowed into identical plastic cylinders. The cylinders are intended to be disposables constructed economically enough to be thrown away after each test.

7 Claims, 6 Drawing Figures

METHOD AND APPARATUS FOR MEMBRANE FILTER STERILITY TESTING

FIELD OF THE INVENTION

This invention relates in general to testing of pharmacological products and more particularly to a disposable device and to a method for membrane filter sterility testing.

BACKGROUND OF THE INVENTION

In the production of pharmacological products of various types such as antibiotics, federal regulations in the United States and similar regulations in other nations require sterility testing to ensure that the products are substantially free of microorganisms such as bacteria, fungi and molds. In the past two methods have been used to carry out such sterility testing.

In one method referred to as the direct method, the product material to be tested is inoculated into a medium that has been prepared and tested to ensure optimum conditions for the growth of the specific contaminant organisms being tested for. Such systems are somewhat limited in that they require a specific volumetric to area ratio, in order to control the oxygenization of the media and these volumetric ratios are sometimes difficult to achieve in practice.

The second method involves the use of a membrane filter as a screen employed to strain and concentrate the contaminant microorganisms from the test product. Thereafter the membrane filter is divided into a number of portions equal to the number of culture media used and each portion is immersed into one culture medium for incubation at a specified temperature for a predetermined period. When the incubation period has been completed the presence of an unduly high level of the contaminant organism in the test product is determined by observation of color changes or turbidity in the incubated culture medium. Typically, for bacteria, a thioglycollate medium has been utilized, which includes a resayurin additive to provide for color indication, and also agar to inhibit diffusion throughout the medium. Immediately after immersion of the filter, this medium is exposed to air until the upper ⅓ of the solution turns pink, indicating oxidation of that portion of the culture medium. Since the agar gel prevents diffusion of the oxidized fluid throughout the culture medium, the result is that the upper portion of the medium provides an environment which promotes the growth of aerobic bacteria, while the lower part of the medium fosters the growth of anaerobic bacteria.

A fluid which has particularly been useful for determination of the presence of fungi is soybean-casein digest medium. Another material which is utilized for this latter purpose is sabourin. By inclusion of surfactants in the media, pharmacological products which include oils or petroleum may be tested. If the pharmacological product is a powder, it may be dissolved in a suitable sterile solution and the resulting liquid is then treated in the same manner as would be a liquid product.

It has been found that in large scale production processes these testing methods are awkward and expensive. For example, the requirement of maintaining sterility while dividing the filter material into two separate portions before introducing it into the media for testing is difficult, as is also the requirement that great care must be taken at each step of the process not to introduce any contaminant microorganism overexposure to the media.

SUMMARY OF THE INVENTION

In the present invention, sterility testing of the membrane filter type is carried out using a special canister which is formed as a cylinder with two ports at one end and a single port at the opposite end. Each of the ports is provided with a cap to allow it to be hermetically sealed when the cap is in position and to allow the port to be open when the cap is removed. One of the two ports at one end is provided with a hydrophobic microporous filter mechanically supported on either side to allow the flow of air through it in either direction while screening out any microorganisms. A second membrane filter is positioned within the cylinder generally parallel to the end having the two ports and spaced apart form that end. This filter is sealed to the side walls of the cylinder such that test product flowed through an unfiltered port into the canister, passes through the second membrane filter and then out through the single port into the opposite end. Bacteria or fungi contamination within the test product is trapped on the membrane filter. The membrane filter is preferably formed with an annular border of hydrophobic material on at least its upper surface and preferably on both surfaces, in order to prevent wetting of the filter in the area of the seal by the product material.

A pair of canisters as above described are used in a test process in which initially the unfiltered port in the two port end of the canister and the single port at the opposite end of the canister are opened and aliquots of the test material are flowed through both canisters to entrap any bacterial or fungi contamination on the membrane filter contained within each of the cylinders. After these aliquots have been passed through the cylinders, both cylinders are rinsed in a suitable sterile solution to remove any residue of the product material itself. Because of the presence of the hydrophobic annular ring on the filter, the test product does not wet that portion of the filter which might not be able to be thoroughly rinsed. Accordingly, particularly in the case of antibiotic materials, the original test product is not retained on the filter to subsequently migrate toward the center of the filter and inhibit the growth of any bacteria that might be present when the filter is in the suitable culture medium.

When the test product has been passed through the canisters and they have been suitably rinsed, a culture medium, such as thioglycollate, suitable for the growth of bacteria, is flowed into one canister through the unfiltered port at one end, while the single port is capped at the opposite end. The filtered port has its cap removed to vent air out of the canister, while still preventing microorganisms from the environment from entering the canister. When the culture medium has been flowed into the canister, the cap over the filter port is replaced after a sufficient period (in the case of thioglycollate) to allow the upper third of the fluid to be oxidized, a condition indicated by its turning pink. Thereafter the replacement of the cap seals the canister against further aeration and consequently inhibits any further oxidization of the fluid.

In the next step the single port at one end of the second canister is capped and the filtered port is uncapped to allow venting while a second culture medium, such as soybean-casein digest medium, suitable for promoting the growth of fungi is flowed into the second canister. Thereafter the canister is capped at all three ports to allow incubation for an appropriate period at an appropriate temperature. Visual observation of the color or turbidity of the liquid medium then provides for determination of the presence of the contaminant microorganisms in the test product.

DESCRIPTION OF PREFERRED EMBODIMENTS

Figure 1:
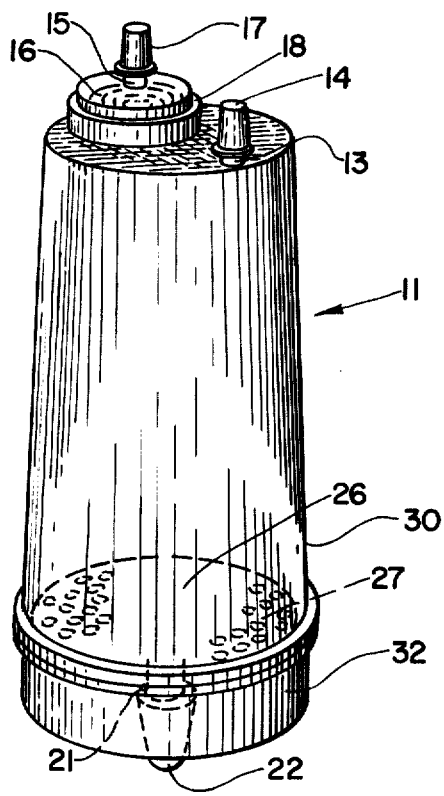
FIG. 1 is an illustration in perspective view of a canister constructed in accordance with the principles of this invention.
Figure 2:
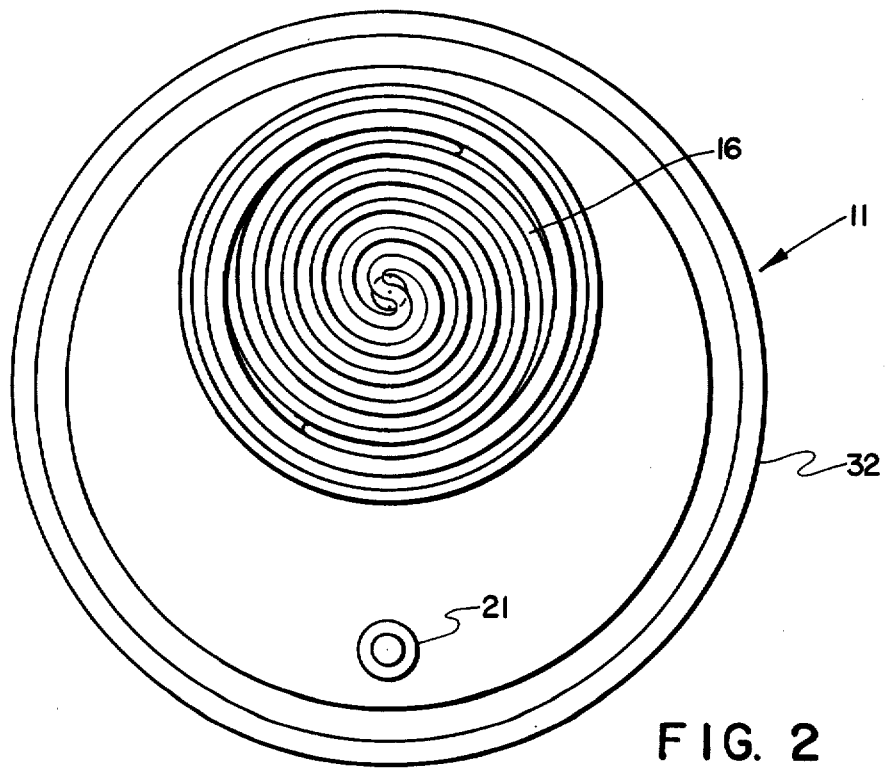
FIG. 2 is an illustration in plan view of the canister of FIG. 1.

With reference now to the drawings, in FIG. 1 a canister for use in sterility testing is illustrated. The canister generally indicated at 11 is formed as a right cylinder, preferably of a transparent material such as clear plexiglass. At one end of the canister 11 there are two ports 13 and 15, each being provided with removable sealing caps 14 and 17 respectively. Port 15 includes a hydrophobic microporous filter, which is mechanically supported on its outer side by support member 16 and on the inner side by a similar support member (not shown). The filter is formed, typically, of cellulose esters coated with a hydrophobic material and performs the function of filtering all microorganisms above a specific size from the air flow through the filter. The porous support member 16 is formed as generally spiral grids (see FIG. 2) allowing air to flow through them, while providing a generally uniform mechanical support for the somewhat fragile filter.

The opposite end of the canister 11, is closed with a base member 32, in which a third port 21 is located and this port is also provided with a removable sealing cap 22. A membrane filter 26 (shown partially broken away) which is substantially the full diameter of the canister 11 is located at the junction between the cylinder wall 30 of the canister 11 and the base member 32. This filter 26 is positioned generally parallel to the ends of the canister 11 and is sealed at its periphery to the wall 30 of the canister, for example by an epoxy cement or by having its edge sandwiched between the wall 30 and the edge of the base member 32 which forms the single pot end of the canister 11. A suitable choice for the filter 26 is a thin (150 $\mu$m) porous membrane of approximately 47 mm diameter composed of biologically inert cellulose esters. The filter preferably is formed with pores 0.45 micrometers in diameter over its surface. Control of the pore size is extremely precise ($\pm$ 0.02 $\mu$m), and no microorganisms larger than the largest pore size are passed by the filter. The filter 26 is desirably formed with a six millimeter annular border in which the surface has been rendered hydrophobic. This may be done, for example, by coating this border with a solution of xylol and silicone.

The purpose for rendering the border hydrophobic is as follows. During operation a test product, such as an antibiotic is passed through the filter 26 to screen out and concentrate microorganisms that may be contained therein. After the passage of the test product, the filter 26 is flushed several times with a sterile solution before inserting the filter 26 itself into a bacterial growth medium. Without the hydrophobic ring, the antibotic absorbed near the edge of the filter 26 is likely not to be completely flushed out and during the incubation period in the culture medium this residue has a tendency to migrate back toward the active center portion of the filter when it could inhibit the growth of the microorganisms thereby rendering the resultant test invalid. The hydrophobic border prevents this portion of the filter from being wet by the initial test product liquid and therefore eliminates the problem of later migration. A filter of this type is available from Millipore Corporation of Bedford, Massachusetts under the designation HAEPO47AW. It is also desirable that the filter covering the port 15 be formed of hydrophobic material to prevent its being wet during the course of operations. A filter of this general type is also available from the Millipore Corporation under the trade designation Fluoropore.

In FIGS. 3 through 6 the utilization of the canister of FIG. 1 in a sterility testing process is shown. In the initial step illustrated in FIG. 3, a tubing 40 with a hypodermic needle 41 is used to draw the product material to be tested from a capsule 43. This liquid is split into aliquots at a Y-shaped stream splitter 43 with one aliquot passing into canister 50 through port 52 and other aliquot passing into canistor 60 through port 62. The filtered ports 54 and 64 respectively of the two canisters are covered with the sealing caps 55 and 65 during this step. The fluid aliquots pass through the membrane filter 57, (in canister 50), and 67 (in canister 60) and are then emptied through aspirating tubes 70 and 71 into a beaker 75 under the influence of vacuum pump 80. Each of the canisters must have its filter port sealed during this step in order to allow sufficient vacuum to be drawn to pull the fluid through the canister. An alternative arrangement during this step would replace the vacuum pump with a peristaltic action pump (not shown) in the line between the ampoule 43 and the canisters 50 and 60. If this pump is a proportional pump a further control on the relative volumes between the aliquots is provided. After the test product has been flowed through the filters, each of the canisters is flushed with a sterile solution, such as sterile water, to flush away all of the product fluid from the canister interior and the filter surface in preparation for incubating the filters in a suitable microorganism growth medium.

Figures 3, 4:
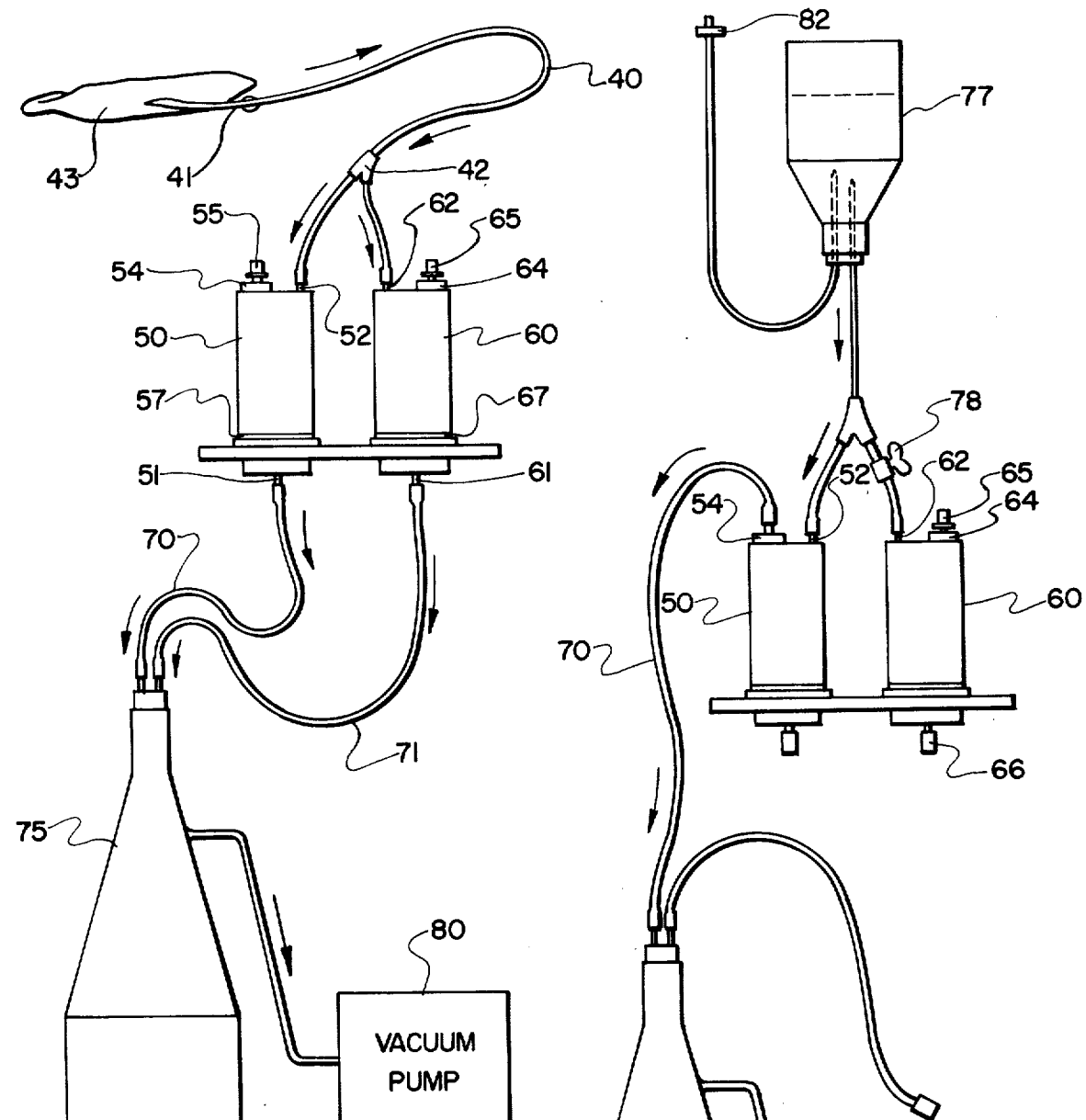
FIGS. 3-6 are illustrations generally in diagrammatic form of a canister arrangement.

A second step of the process is illustrated in FIG. 4 in which the ampoule 43 is replaced with a reservoir 77 containing a suitable microorganism growth medium. For purposes of promoting the growth of fungi, the reservoir 77 in this step may contain, for example, a soybean-casein digest medium. A description of the preparation of such a medium is described in U.S. Pharmacopeia XVIII at Page 852. An alternative material for this purpose is sabourin. The fluid from the reservoir 77 is then flowed into only canister 50 under conditions in which a clamp 78 clamps off the inlet to the unfiltered port 62 in canister 60. The filtered port 64 in the canister is sealed with cap 65 and the single port 61 in the opposite end of canister 60 is sealed off with its cap 66. The growth medium is flowed into canister 50 through port 52 under the influence of vacuum pump 80 which has line 70 now connected to the filtered port 54, thereby providing for venting of the air from canister 50 without the possibility of introducing any bacterial contamination through this vent. The soybean-casein digest medium reservoir 77 is vented through a filtered input 82 thereby preventing any contamination from the outside atmosphere entering this medium.

Figures 5, 6:
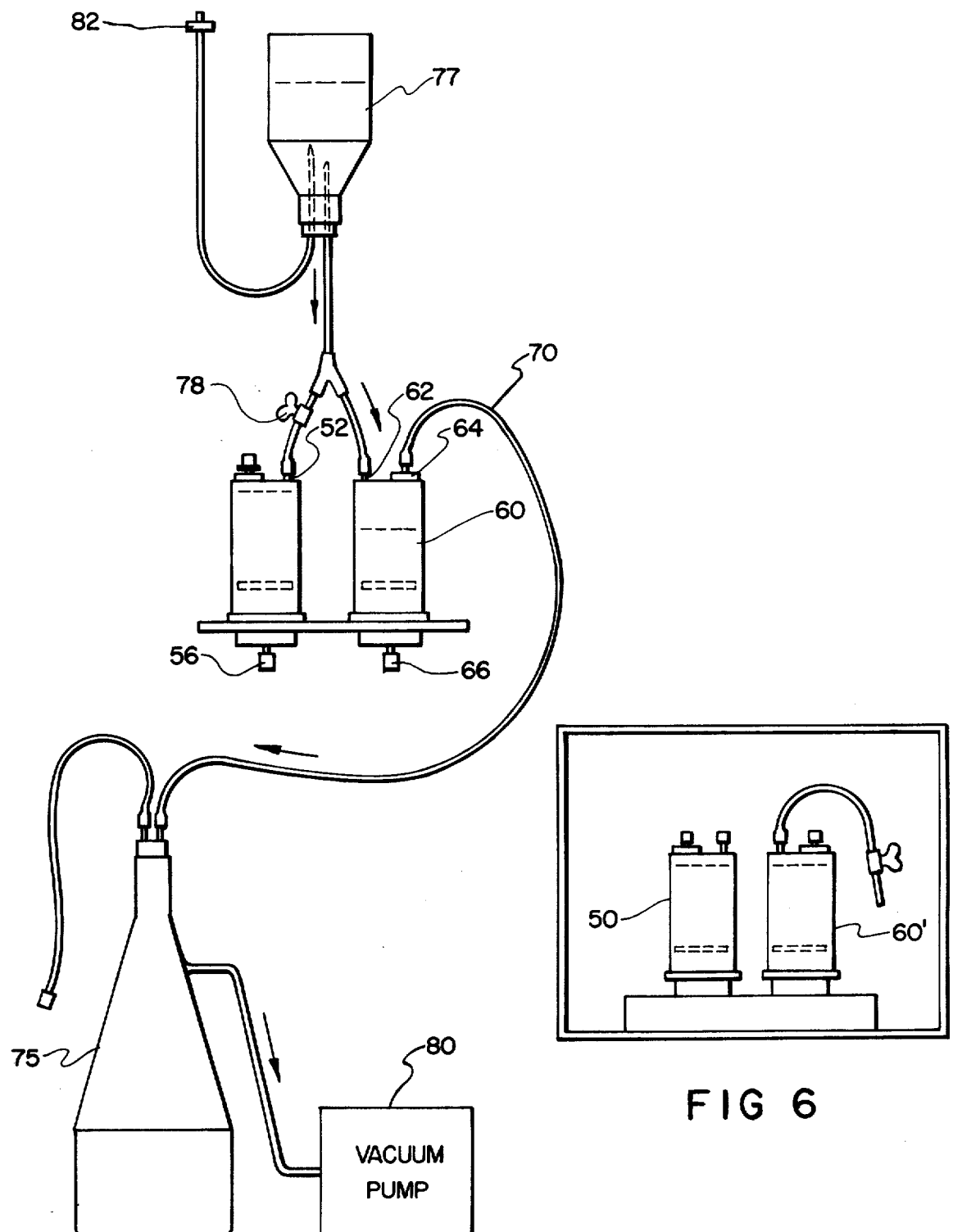

At the conclusion of this second step, the clamp 78 is used to shut off the input flow to port 52 in canister 50 and vacuum pump 80 is connected through aspirating line 70 from the beaker 75 to the filtered port 64 of canister 60 as shown in FIG. 5. The reservoir 77 is now provided with a different microorganism growth medium, particularly suitable for promoting the growth of bacteria. A typical medium for this purpose is a thioglycollate solution, the formulation of which is described in the U.S. Pharmacopeia XVIII at Page 852. Under these circumstances the canister 60 is filled with the thioglycollate medium and, at the conclusion of this filling, the port 64 is left open to vent air into the canister for a sufficient period to allow the upper ⅓ of the thioglycollate medium to become oxidized. This condition is indicated by the liquid turning a pink color. When approximately ⅓ of the fluid has become pink the sealing cap 65 is placed over the port 64 to prevent any further oxidation of the medium. The resultant medium is, in actuality, a three level medium with the upper oxidized region providing a suitable medium for promotion of growth of aerobic bacteria, the central region providing a suitable medium for the growth of faculative aerobes and the lowest third of the volume of the medium providing a suitable environment for the growth of anaerobes.

In the final step as illustrated in FIG. 6, both canisters 50 and 60 are incubated for a period of seven days, with the canister 60 being sealed at all entry ports to prevent any further oxidation of the medium. The thioglycollate medium is maintained at a temperature 30° and 35° Centigrade while the soybean-casein digest medium is maintained at a temperature between 20° and 25° Centigrade. If, at the conclusion of this period, no turbidity is observed in the solutions, the product material was free from the contaminant microorganisms.

As in any sterility test system, a control is run in which a sterile control fluid is substituted for the test product and the entire procedure including the medium are processed in the same fashion as for the actual material to be tested. If at the conclusion of the incubation period, microorganism growth has been observed in either of the canisters, a review of the details of the procedure must be carried out to ascertain the source of contamination. Upon conclusion of the procedure the canisters 50 and 60 may be disposed of in any suitable manner, since they are made of relatively inexpensive plastic materials.

While specific embodiments have been described, it will be understood that other materials may in many instances be substituted and the invention should be construed as limited only by the scope of the appended claims.

We claim:

1. A method of testing for sterility of a liquid test material comprising the steps of:
   first, providing an aliquot of said test material to each of first and second substantially identical canisters, each of said canisters having first and second ports in a first end thereof and a third port in the opposite end thereof and each of said canisters having a filter support member positioned within said canister parallel and spaced from said first end thereof and a second membrane filter supported on said filter support member, said second membrane filter facing said first canister end and sealed to the walls of said canister, said first port including a first membrane filter in it to provide that air flowing through said port has any microorganism above a predetermined size carried therein screened by said first filter, said first port being capped during said first step to provide a substantially hermetic seal and said second and third ports being opened to provide for passage of fluid through said canister whereby microorganisms in said test material are deposited on the second membrane filters within said canisters,
   second, flushing each of said canisters with sterile solution with said ports in the same condition as during said first step to remove all of said test material from said second membrane filter, except for bacteria which has been trapped on said filters,
   third, sealing said third port on the first one of said canisters while leaving said first port open and providing through said second port a known volume of a first microorganism growth medium;
   fourth, sealing said third port of the second one of said canisters, while leaving said first port of said second of said canisters open and providing through said second port a known volume of a second mircoorganism growth medium, and
   fifth, sealing all three of said ports to said canisters while maintaining the canisters in a specified range of temperatures for predetermined periods to allow bacterial growth in said first and second media, said media being formulated such that the growth of bacteria above a predetermined amount effects a visually measurable change in the appearance of the fluid within said canisters.

2. A method in accordance with claim 1 wherein said first growth medium is a thioglycollate solution.

3. A method in accordance with claim 2 wherein said second growth medium is soybean-casein digest medium.

4. A process in accordance with claim 2 wherein said second medium is sabourin.

5. A process in accordance with claim 2 wherein said thioglycollate solution includes a color indicator to indicate oxidized portions of said medium.

6. A process in accordance with claim 3 wherein said first canister is held at a temperature between 30° C and 35° C for seven days and wherein said second canister is held at a temperature between 20° C and 25° C for seven days.

7. A process in accordance with claim 5 wherein at the conclusion of said third step said first port is left open for a sufficient period to allow said thioglycolate solution in the upper third of said canister to change color.

* * * * *